(12) United States Patent
Kovarik et al.

(10) Patent No.: US 8,936,030 B2
(45) Date of Patent: *Jan. 20, 2015

(54) NAIL POLISH REMOVER METHOD AND DEVICE

(71) Applicants: Katherine Rose Kovarik, Englewood, CO (US); Joseph E. Kovarik, Englewood, CO (US)

(72) Inventors: Katherine Rose Kovarik, Englewood, CO (US); Joseph E. Kovarik, Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/307,651

(22) Filed: Jun. 18, 2014

(65) Prior Publication Data

US 2014/0290683 A1 Oct. 2, 2014

Related U.S. Application Data

(63) Continuation-in-part of application No. 14/079,054, filed on Nov. 13, 2013, now Pat. No. 8,757,173, which is a continuation of application No. 13/425,913, filed on Mar. 21, 2012, now Pat. No. 8,584,685.

(60) Provisional application No. 61/467,767, filed on Mar. 25, 2011.

(51) Int. Cl.
*A45D 29/00* (2006.01)

(52) U.S. Cl.
CPC .............. *A45D 29/007* (2013.01); *A45D 29/00* (2013.01)
USPC .......................... 132/200; 132/74.5; 132/285

(58) Field of Classification Search
USPC .......... 132/200, 73, 73.5, 74.5, 285, 319, 320
See application file for complete search history.

(56) References Cited

U.S. PATENT DOCUMENTS

| 3,014,579 | A | * | 12/1961 | Lathrop | 401/196 |
| 3,124,825 | A | * | 3/1964 | Iovenko | 15/104.93 |
| 3,341,466 | A | | 9/1967 | Brynko et al. | |
| 3,369,553 | A | | 2/1968 | Keesee | |
| 3,516,941 | A | | 6/1970 | Matson | |
| 3,577,515 | A | | 5/1971 | Vandegaer | |
| 3,598,685 | A | | 8/1971 | Lee et al. | |

(Continued)

FOREIGN PATENT DOCUMENTS

| EP | 0385534 | 9/1990 |
| GB | 751600 | 6/1956 |
| WO | WO 03/101606 | 12/2003 |

OTHER PUBLICATIONS

"Magis™ Foil Nail Wraps—Products," Magis Supplies Ltd., 2013, [retrieved on Dec. 30, 2013], 2 pages. Retrieved from: www.foilnailwraps.com/products.

(Continued)

*Primary Examiner* — Robyn Doan
*Assistant Examiner* — Tatiana Nobrega
(74) *Attorney, Agent, or Firm* — Sheridan Ross P.C.

(57) ABSTRACT

Nail polish remover strips are pre-sized for toe or fingernails and applied to a painted or artificial nail and left thereon for a predetermined period of time to dissolve the nail polish and/or nail bonding agent. Preferably a color change occurs to depict the appropriate dwelling time to dissolve the nail polish. Certain embodiments include odor reducing components. Preferably the strips are layered composites having an exterior odor impervious material, a layer of encapsulated acetone or nail polish removing agent, an absorbent layer, and a peelable backing, with the strips being curved to accommodate contact with a person's nail.

18 Claims, 9 Drawing Sheets

(56) References Cited

U.S. PATENT DOCUMENTS

| | | | |
|---|---|---|---|
| 3,645,835 A | 2/1972 | Hodgson | |
| 3,729,569 A * | 4/1973 | Charle et al. | 424/401 |
| 3,759,259 A | 9/1973 | Truhan | |
| 4,619,253 A | 10/1986 | Anhauser et al. | |
| 4,696,393 A | 9/1987 | Laipply | |
| 4,740,194 A | 4/1988 | Barabino et al. | |
| 4,800,904 A * | 1/1989 | Kinseley et al. | 132/73.5 |
| 4,844,885 A * | 7/1989 | Chernack | 424/61 |
| 4,938,347 A | 7/1990 | Tillman | |
| 5,026,541 A | 6/1991 | Lanier | |
| 5,066,419 A | 11/1991 | Walley et al. | |
| 5,100,028 A | 3/1992 | Seifert | |
| 5,154,842 A | 10/1992 | Walley et al. | |
| 5,320,217 A | 6/1994 | Lenarz | |
| 5,415,903 A | 5/1995 | Hoffman et al. | |
| 5,455,043 A | 10/1995 | Fischel-Ghodsian | |
| 5,525,389 A | 6/1996 | Hoffmann et al. | |
| 5,558,700 A | 9/1996 | Shibahashi et al. | |
| 5,591,820 A | 1/1997 | Kydonieus et al. | |
| 5,656,282 A | 8/1997 | Cook et al. | |
| 5,823,203 A | 10/1998 | Carroll et al. | |
| 5,924,428 A | 7/1999 | Song | |
| 6,016,915 A | 1/2000 | Almond | |
| 6,020,066 A | 2/2000 | Weisser et al. | |
| 6,060,073 A | 5/2000 | Keller | |
| 6,305,383 B1 | 10/2001 | Thoma | |
| 6,367,485 B1 * | 4/2002 | Dutton-Davis et al. | 132/200 |
| 6,394,040 B1 | 5/2002 | Axel | |
| 6,405,735 B1 * | 6/2002 | Dockery | 132/74.5 |
| 6,481,443 B1 | 11/2002 | Moore-Johnson et al. | |
| 6,534,079 B1 | 3/2003 | Munagavalasa | |
| 6,582,714 B1 | 6/2003 | Emmrich et al. | |
| 6,586,529 B2 | 7/2003 | Mumick et al. | |
| 6,634,367 B2 * | 10/2003 | Abraham et al. | 132/74.5 |
| 6,662,807 B2 | 12/2003 | Meinschewnk | |
| 6,865,444 B2 | 3/2005 | Howard | |
| 6,901,935 B2 | 6/2005 | Chang | |
| 6,988,502 B2 | 1/2006 | Tsukamoto | |
| 6,990,985 B1 | 1/2006 | Allen et al. | |
| 7,008,392 B2 | 3/2006 | Beaudry | |
| 7,025,521 B2 | 4/2006 | Tsaur | |
| 7,806,877 B2 | 10/2010 | Kang et al. | |
| 7,980,203 B1 | 7/2011 | Rubottom et al. | |
| 8,513,322 B2 * | 8/2013 | Wright et al. | 522/153 |
| 8,534,947 B2 | 9/2013 | Prax | |
| 8,584,685 B2 | 11/2013 | Kovarik et al. | |
| 8,696,227 B1 | 4/2014 | Carter | |
| 8,748,477 B2 | 6/2014 | Scialdone | |
| 8,757,173 B2 | 6/2014 | Kovarik et al. | |
| 2002/0160035 A1 | 10/2002 | Fotinos | |
| 2003/0125222 A1 | 7/2003 | Jahns et al. | |
| 2003/0127104 A1 | 7/2003 | Tyre | |
| 2004/0134999 A1 | 7/2004 | Aiyama | |
| 2004/0142830 A1 | 7/2004 | Tavares | |
| 2005/0284777 A1 | 12/2005 | Wilkman | |
| 2006/0188538 A1 | 8/2006 | Emmrich et al. | |
| 2006/0226249 A1 | 10/2006 | Ketcha et al. | |
| 2006/0283470 A1 | 12/2006 | Keogh | |
| 2007/0107745 A1 | 5/2007 | Kiyomoto | |
| 2007/0287647 A1 | 12/2007 | Hadry | |
| 2008/0039812 A1 | 2/2008 | Kang | |
| 2008/0041404 A1 | 2/2008 | Vo | |
| 2008/0060550 A1 | 3/2008 | MacDonald | |
| 2008/0142405 A1 | 6/2008 | Knapp | |
| 2010/0083974 A1 | 4/2010 | Milican | |
| 2010/0175942 A1 | 7/2010 | Griep et al. | |
| 2010/0204076 A1 | 8/2010 | Cheng | |
| 2010/0275942 A1 * | 11/2010 | Barile | 132/200 |
| 2010/0305491 A1 | 12/2010 | Bschnagel | |
| 2011/0152159 A1 | 6/2011 | Labeque | |
| 2011/0284017 A1 | 11/2011 | Nakamura | |
| 2012/0148636 A1 | 6/2012 | Berrido et al. | |
| 2012/0264788 A1 | 10/2012 | Ecker et al. | |
| 2012/0305019 A1 * | 12/2012 | Barile | 132/200 |
| 2013/0074859 A1 * | 3/2013 | Horvath et al. | 132/73.5 |
| 2013/0095162 A1 | 4/2013 | Quinn | |
| 2013/0247841 A1 | 9/2013 | Stoffels et al. | |
| 2013/0251773 A1 | 9/2013 | Galiatsatos et al. | |

OTHER PUBLICATIONS

Official Action for U.S. Appl. No. 13/425,913 mailed Feb. 15, 2013, 11 pages.

Notice of Allowance for U.S. Appl. No. 13/425,913 mailed Sep. 16, 2013, 14 pages.

Notice of Allowance for U.S. Appl. No. 14/079,054 mailed Feb. 7, 2014, 9 pages.

* cited by examiner

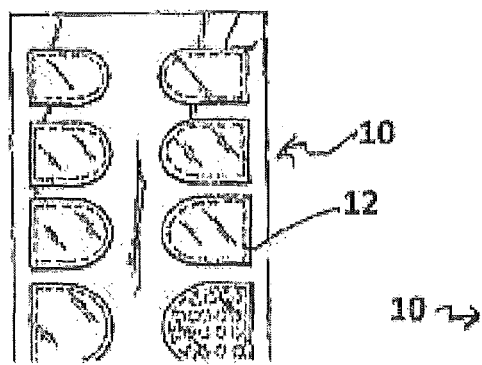
FIG. 4
FIG. 5
FIG. 3

NAIL POLISH REMOVER METHOD AND DEVICE

RELATED APPLICATIONS

This application is a continuation-in-part of U.S. patent application Ser. No. 14/079,054 filed on Nov. 13, 2013 (now U.S. Pat. No. 8,757,173, issuing Jun. 24, 2014), which is a continuation of U.S. patent application Ser. No. 13/425,913 filed on Mar. 21, 2012 (now U.S. Pat. No. 8,584,685, issued Nov. 19, 2013), which claims priority from U.S. Provisional Patent Application No. 61/467,767 filed on Mar. 25, 2011. The entire disclosure of the prior applications are considered to be part of the disclosure of the accompanying application and are hereby incorporated by reference.

FIELD OF THE INVENTION

The present invention relates to nail polish remover strips, and more particularly to fingernail and toe nail sized tabs or strips that can be applied to a painted or artificial nail and left thereon for a predetermined period of time to dissolve the nail polish and/or nail bonding agent.

BACKGROUND OF THE INVENTION

Fingernail polish and artificial fingernails are in widespread use as cosmetic enhancements, and are applied by the consumer as well as by professionals in salons. Artificial fingernails are typically produced either by gluing on pre-manufactured acrylic fingernails, or built up using an artificial fingernail form to apply layers of acrylic materials that are shaped to form an artificial fingernail. Although modern materials and methods enable very real looking artificial fingernails to be produced, it is necessary to periodically repair or remove the artificial fingernails. Artificial nails such as, for example, acrylic, gel or silk, linen or fiberglass wraps, have become popular and such products are applied or bonded onto the natural nail to provide a uniform appearance and then a nail polish or lacquer is applied to provide color and/or to cover the sculpting product used to form the artificial nail. Nail polish or lacquer products are applied as a temporary decoration and/or to improve the strength of the underlying nail. Such nail polishes or lacquers are removed using commercially available solvents in the form of nail polish removers.

Changing or removing a colored polish or lacquer from artificial nails can be difficult since most commercially available nail polish removers may damage the underlying sculpting product.

Artificial fingernails and fingernail polish are generally removed by immersing the wearer's fingertips in a solvent to soften and dissolve the polish and the glues and acrylics comprising the artificial fingernails. Acetone is generally used as the solvent. Acetone is a volatile material and evaporates quickly, producing gaseous compounds that may irritate the throat, lungs and eyes of exposed individuals. Further, acetone may damage adjacent furniture, carpet and other objects if it is spilled or splashed onto these surfaces. Exposure to the gaseous compounds resulting from use of acetone generally does not pose a problem for the average consumer, since the consumer is only relatively infrequently exposed to these compounds. However, professional manicurists and beauticians may be exposed to acetone on a daily basis. Over time, contact with acetone can pose a serious health hazard.

Various devices have been developed in the prior art in order to facilitate the removal of fingernail polish and artificial fingernails, and especially to reduce the hazards associated with the use of strong solvents to remove the fingernail polish and artificial fingernails. Many of these prior art device utilize covers to minimize evaporation of the solvent and to minimize exposure of the manicurist or wearer to the solvent. Other devices include sponges, brushes or other scuffing materials to hasten softening and removal of the fingernail polish and/or artificial fingernails.

The task of removing nail polish typically involves administering the nail polish remover onto a human nail or artificial nail through the use of a cotton ball and rubbing the cotton ball containing nail polish remover on the human nail or artificial nail until the nail polish has been removed. Soaking in such solutions is often employed, exposing not only the finger or toenail surface but also the surrounding skin regions that never had any polish associated therewith. Absorbing such agents into the skin around the nail is something many wish to avoid. Methods of removing nail polish or false nails is often an arduous and messy procedure. There is a long felt but unsolved need for an inexpensive, easy safe and repeatable way to remove nail polish and artificial nails, especially one where both the customer and the nail professional are not unduly exposed to the often unpleasant and unhealthy odors, fumes and smells of nail polish removal substances.

Accordingly, there is need for a method and apparatus for removing fingernail polish and artificial fingernails simultaneously from plural fingers, which is simple and inexpensive to manufacture, and which may be easily and comfortably used to remove fingernail polish and/or artificial fingernails from a wide range of different size hands.

SUMMARY OF THE INVENTION

The present invention is directed to nail polish removing strips that can be applied to the surface of a polished nail and remain there until the polish is dissolved sufficiently to have it removed. In one embodiment a color change is relied upon to signal to a person that the strip has been in place on the polished nail (or artificial nail) for a sufficient and predetermined time, namely a time sufficient to permit the chemical dissolution of the polish or adhesives sought to be removed from the person's nail.

The present invention in certain embodiments includes either an acetone based solution to remove nail polish or non-acetone based polish removers. Solvents such as acetates, acetones and acetonitriles can weaken and/or dissolve the resins or sculpting products used to form and/or bond the artificial nail to the natural nail. In other contexts, there is a need to remove polish from artificial nails without damaging or compromising the integrity of the resins or sculpting products used to form the artificial nail. Such a nail removal substance is retained primarily in a pad or absorbent region that is positioned next to a person's nail for a predetermined period of time sufficient to largely or completely remove polish associated with the nail. The removal substance is preferably contained in-between an outer odor reducing layer and a removable strip laminate. Once removed, the strip laminate thus exposes the nail polish removing saturated pad to the nail polish surface. Preferably adhesive is employed to maintain the strip in place for a predetermined time to permit the nail polish to be dissolved. Such adhesive may be provided along the periphery of the strip so that the majority of the nail contacting surface does not have adhesive—and so that the adhesive is not also dissolved prior to the strip being in pace for the desired amount of time. In other embodiments a color change is relied upon to signal to a person that the strip has been in place on the polished nail (or artificial nail) for a sufficient and predetermined time. Such color change can be for the entire strip; it may be for a portion of the strip (e.g. such as a portion that is not also involved in the provision of nail polish removing material to the nail—and thus is merely associated with the removal of the bottom laminate to trigger a time frame within which a color change will occur. The purpose of the color change is to warn a person that the nail polish removal substance or agent has been in place a predetermined period of time.

The type of amount of nail polish remover that can be used with the present invention can vary depending on many factors, such as a preference, whether there is a sensitivity to any particular agent, etc. As for non-acetone remover compositions, one alkyl nitrite solvent that is suitable includes isobutyl nitrite. Isobutyl nitrite has the chemical formula $C_4H_9NO_2$ and can be alternatively referred to as nitrous acid, isobutyl ester; nitrous acid, 2-methylpropyl ester; and IBN. Isobutyl nitrite is very stable and has a moderate toxicity level. In particular, isobutyl nitrite has an inhalation toxicity level of about 600 ppm in vapor which makes it less toxic than previous nail polish removers. For example, acetonitrile, which has an inhalation toxicity level of about 60 ppm in vapor, is ten times more toxic than isobutyl nitrite. Thus, in accordance with certain embodiments, a vapor phase of the nail polish remover suitably includes less than about 600 ppm isobutyl nitrite.

Isobutyl nitrite has a pleasant and fruity odor. Preferably, the nail polish remover includes isobutyl nitrite that is greater than or equal to about 20% pure isobutyl nitrite, and even more preferably includes isobutyl nitrite greater than or equal to about 50% pure isobutyl nitrite, and even more preferably at least about 80% to about 95% by volume isobutyl nitrite. Nail polish removers generally contain acetone, acetonitriles, benzene, aromatic nitrites, alcohol and/or ethyl acetate as the active ingredient. Still others comprise ethyl acetate, acetone and/or acetonitrile-free nail polish remover containing isobutyl nitrite and butylated linseed oil for removing nail polish.

Still other non-acetone containing nail polish removers have a reduced level of toxicity and a more pleasing odor.

Compositions included with the present invention include a hygroscopic stabilizer to reduce degradation of the nail polish remover and/or individual components or ingredients in the nail polish remover upon exposure to aqueous media. In preferred embodiments, the nail polish remover includes or contains about 0.25% to about 2% by volume hygroscopic stabilizer, such as butylated linseed oil. It can also include one or more inactive ingredients such as sodium bicarbonate, silicone, isobutyl alcohol, calcium chloride, and water. a plastic sleeve containing glass ampoule, or similar tool.

In one embodiment, a strip of the present invention is contacted with a polished nail for a period of at least about 3 minutes, more preferably at least about 5 minutes, and less than about 10 minutes.

Preferably the strips have both desired adhesive qualities so that they remain in place on a nail for the desired period of time, as well as having the polish-dissolving abilities conferred by the active agents, such as acetone or non-acetone polish removing compositions.

In one particular embodiment, clear or substantial transparent strips have either acetone or non-acetone compositions provided with either both sides of a dual-layered strip (with polish removing compounds provided therebetween) and the strip is positioned on the surface of a nail to permit the polish removing composition to dissolve nail polish it comes into contact with. In one particular embodiment, when clear nail polish is removed, a color change agent or indicator is provided so that after about 5 minutes of contact between the strip and the polished nail, there is a color change sufficient to indicate to the person to whom such strip has been applied to appreciate that such time period has passed and is presumably sufficient to have removed and/or substantially dissolved the nail associated polish. In certain embodiments, the top most cover contains a color change agent such that when the acetone beads are crushed, thereby releasing the acetone into the below absorbent pad, the acetone also reacts with color change agents associated with a top cover and/or the absorbent pad, such that a user can discern a color change after a predetermined amount of time. Such time period can be set through adjusting chemical reaction between the acetone and a color change agent such that, for example, after about five minutes, the color change takes effect so that a user will appreciate and notice that such time period has expired and thus the nail polish removing device should be detached from the person's nail to thereby avoid any unpleasant and/or undesired further contact between the person's nail/skin and the acetone (or any other nail polish removing agent). One of skill in the art will appreciate that the top cover of the device as pictured in FIG. 6 can be transparent and/or in itself may be of a particular color. Preferably, the top most cover is substantially transparent such that not only the crushing and frangible nature of the nail polish containing beads can be discerned (thus ensuring that substantially all beads are crushed to release the nail polish removing material), but such transparency also facilities detecting the timed color change after a predetermined amount of time from the fracturing of the nail polish containing beads and the reaction with the color change agent. One of skill in the art will appreciate that the color change agent can again be associated with the top cover, the absorbent pad, the layer upon which nail polish removing beads are affixed, or otherwise. The important aspect is that a color change is perceived at a predetermined time and this aspect of the present embodiments provides a built in safety feature so that the strips are not misused, either consciously or unconsciously by a user or professional nail cosmologist. One will also appreciated, however, that other color changing methods and devices can be employed in association with various aspects of the present invention. For example, the top cover can in addition contain a layer that once removed changes color in about five minutes, whether or not such color change is directly associated with a chemical reaction with a nail polish removing substance, such as acetone.

A reagent, such as sodium nitroprusside may react with an acetone or an associated component, such as typically acetoacetic acid, to form a purple complex with the reagent. A reagent color change from pink to shades of increasingly dark purple provides a rough quantitative measure of acetone. The reactive ingredients of the reagent may be, for example, urease and bromthymol blue under a permeable membrane. The urease reacts with the urea to hydrolyze the urea to carbon dioxide and ammonium hydroxide. The liberated ammonium hydroxide increases the pH and the shift in alkalinity is indicated by the change in hue of the bromthymol blue. To achieve the range desired, the reagent zone may be impregnated with 3.2 I.U. of urease and 33 mcg. bromthymol blue. A non-reactive yellow dye may also be added to the reagent to provide a convenient color scale change from yellow through green to dark blue-green for comparison with a color block grid.

As depicted in certain of the figures, in a preferred embodiment the nail polish removing strips and/or pads are individually curved so as to approximate the curvature of a person's nails. This facilitates a more rigid provision of nail polish removing strips or pads and avoids the undesired planar or flat nature of a pad that may detract from desired surface contact with a person's nail once in place. Preformed curved pads or strips also may eliminate or reduce the need for adhesives to secure the nail polish removing strips or pads for the predetermined amount of time that contact is required with a person's nail to remove nail polish associated therewith. In other words, the curvature of the pad or strip itself may facilitate placement and retention of the nail polish removing device on the nail even without any application of any adhesive. In still other embodiments, placement and retention of the nail polish removing device on the nail even without any application of any adhesive. In still other embodiments, rubber bands, bandages, or other adhesive devices can be employed in addition to the present device to secure individual strips or pads around a person's finger or toe if a more secure attachment is desired. In still other embodiments, the strips are flexible and/or deformable so that they maintain a desired curve once applied to a nail, thus assisting in holding the strip in contact with the nail, either with or without adhesives.

The typical need to rub acetone repeatedly on a polished nail to remove undesired old polish is difficult if not impossible for older adults. Thus, such individuals are compelled to have another person, typically a professional pedicurist or nail salon employee, thus resulting in a more expensive endeavor. Thus, there is a need for more aged or less flexible adults to remove nail polish off of their toes in a fashion that does not involve the sustained contortions typically required to rub cotton balls soaked in acetone or other polish removal agents on one's toenails.

In certain embodiments, the ease of a person being able to travel with a self-contained system that permits them to remove shellac and gel nail products is facilitated by providing an acetone impermeable material, such as foil, associated with an absorbent layer that is soaked with acetone (or other effective solvent) at a time at or shortly after the nail of the person is contacted by the absorbent material. Instead of having to carry with them a separate bottle of acetone, cotton balls, foil, etc. the present invention provides a way to avoid the hassle, mess, and need for various separate materials to accomplish the simple task of removing material from a person's nails. As one will appreciate, the manner in which the soaked absorbent material is held in close contact with the nail for the desired period of time can vary, such as by having the toe or finger wrapped by the foil with the saturated absorbent material being held in contact with the nail, or alternatively by having an adhesive region that adheres the impermeable material (e.g. foil) to particular portions of the person's nail surrounding tissue. In certain embodiments there are provided structural barriers that preclude the ability of acetone/solvent to reach adhesive regions around the nail itself, thus limiting the prospect that the foil band-aide-like material will fall off the person's nail prior to the pre-determined time required for the acetone/solvent to dissolve the gel/shellac, etc. on the nail's surface. For example, a crease or small wall structure, or both, in the impermeable materiel can be provided such that the acetone that soaks the absorbent material will be directed by the physical structures such that the dissolving abilities of the solvent/acetone are directed away from the adhesive regions and otherwise substantially precluding the migration of the solvent/acetone to travel to the adhesive contacting regions adjacent the nail. In certain embodiments, a foil wrap having an absorbent material associated therewith (e.g. by bonding to the foil, glued, etc.) has an ampoule—or more preferably a popule—filled with a solvent, such as acetone, associated with the absorbent material—preferably by being in-between the foil and the absorbent material, but may also be glued or otherwise attached to the absorbent material—or a region adjacent to the absorbent material. By "popping" the popule filled with solvent, the absorbent material is saturated sufficiently to provide a shellac and gel removing agent that is permitted to reside on the surface of the person's nail for a desired period of time to effectively dissolve the material present on the nail. In a preferred embodiment, the popule has two different compartments such that a color change agent is released from one compartment when the popule is popped, thus initiating a predetermined time period prior to a perceptible color change to be perceived by a use.

In still other embodiments the encapsulation of the acetone/solvent is achieved via the enclosure of both the acetone/solvent and the associated absorbent material, rather than merely the solvent/acetone itself. Thus, in a particular embodiment, a foil nail-sized material has an acetone saturated absorbent material associated and in contact with the foil, the acetone prevented from evaporating by encapsulating the saturated surface of the material with an acetone impermeable material, such as another portion (or folded) of foil material. In one embodiment, two foil portions, with a saturated acetone absorbent material therebetween, is sonically and/or heat sealed together, such that the two foil portions encapsulate the saturated acetone absorbent pad in a fashion such that the acetone does not evaporate, but rather is encapsulated within the foil enclosure. Opening such enclosure, via pulling apart the foil material portions apart to provide one foil portion having the acetone saturated absorbent material associated therewith, thus enabling the saturated absorbent material to be sufficiently wet so that material on the nail surface can be dissolved within a predetermined time. While gluing an acetone saturated absorbent pad to foil poses some practical problems, there are other ways to position the soaked acetone pad in a desired position adjacent the foil material, such as by structurally providing a perforated foil pocket within which the acetone saturated pad can reside, with acetone able to traverse through the perforations in the foil pouch material when placed adjacent the nail surface. In addition to foil, other suitable materials to constrain acetone, such as rigid polyethylene, conventional polypropylene, polyvinylchloride, and polytetrafluoroethylene. As depicted in FIGS. 3-8, one of skill in the art will appreciate the vast variety of structures that can be produced via the guidance provided herein, where a sufficient and desired and/or effective amount of acetone (or other suitable solvent) is included in an encapsulated enclosure, such as one made from an acetone resistant material, to achieve the function of removing nail polish, removing gel shellac and/or artificial nail surfaces.

In terms of amount of acetone, it is believed that at least about 0.5 ml and preferably around 1 ml is what works best for most removal procedures. More acetone than can be readily employed to coat the nail and remove gel or shellac, etc. from the nail, threatens to cause unnecessary leakage, dripping of acetone, as well as presents the difficulties associated with the acetone reaching any adhesive portion of the device, thus either making the glue tacky or worse, potentially non-effective. In various embodiments, the adhesive, even if contacted eventually (e.g. over the approximately 10 or so minutes required to remove conventional shellac or gel coatings,) will remain sufficiently tacky so that the nail contacting portions remain effective and in place, despite the increasing tackiness (and thus slow decline of the adhering abilities of the adherent material associate with the device.)

In certain embodiments, a foil wrap structure suitable for wrapping around a person's finger, is provided with a stamp sized (e.g. fingernail sized) portion of absorbent material, such as sun laced fabric, plastic weave material (preferably suitable for use with acetone) or cotton, and an encapsulated vial, ampoule, capsule (much like a gel capsule for Advil™), popule, etc. is associated adjacent to the absorbent material. Incorporated herein by this reference is U.S. Patent Publication No. 20130074859 to Schaeffer et al., illustrating a type of foil wrap suitable for various embodiments. The association may be via adhesive bonding, but may also be via a physical pocket formed in the absorbent material that can contain at least the majority of the encapsulated solvent material in a manner such that the capsule, for example, it restrained in association with the absorbent material. While in preferred embodiments, the capsule (which will be understood to be employed herein as an example of other similar structures) is pre-associated with the absorbent material upon manufacture of the individual nail strips as described herein, other embodiments include the ability for an end-user to place the capsule near the absorbent material just prior to us, such as placing the capsule of solvent inside a pre-formed pocket in the absorbent material, designed to retrain the capsule. After the capsule is positioned next to the absorbent material, the foil wrap material is placed around a person's nail surface such that the absorbent material, now having the capsule residing in such pocket (or otherwise associated therewith), positioned just above and in contact with the surface of the nail.

The foil wrap material is then secured in place to the person's finger by one of several ways, such as by simply wrapping the foil around the finger, thus securing it to the person's finger so that it cannot easily fall off; by having another stricture member associated around the foil such that it is secured to the person's nail; and most preferably, by having an adhesive portion around at least the periphery of the nail region such that the foil can adhere to the skin regions adjacent the person's nail, preferably on at least two opposite sides of the person's nail region, more preferably on three sides (i.e. opposing sides and the bottom of the nail region); and in some embodiments, also including the top portion region of a person's nail. Preferably the adhesive is placed on the foil material such that a person employing such strips can still readily manipulate a magazine or book or iPad or phone, etc. without difficulty. Thus, while wrapping a person's individual fingers with foil so as to secure the capsule containing solvent in close association with the person's nail, such wrapping of the finger causes some discomfort and is awkward when one is trying to read a magazine, etc. thus, one advantage of certain embodiments is that by having adhesive placed strategically about the nail region, the absorbent material with the solvent-containing capsule associated therewith, is positioned effectively against the nail surface and is held in place sufficiently securely, for the desired time it takes to permit the solvent to do its function, once it is released from the capsule. Although the use of certain solvents, such as acetone, is likely to dissolve the adhesive that is provided around the periphery of the nail region, the vast majority of the solvent, via the construction of the absorbent material, as well as other solvent blocking structures that can be included, suffice to permit the strip to reside on the surface of the nail for a sufficient period of time, e.g. at least about 3 minutes, more preferably at least about 5 minutes and more preferably at least about 10 minutes, such that the solvent dissolving work and purpose of the solvent on the nail surface is achieved prior to the strip being displaced from the surface of the nail.

The manner in which a capsule can be fractured in order to release its solvent contents is variable and will be understood by those of skill in the art. Preferably, the capsule is constructed in a manner that it is sufficiently robust such that mere transport and packaging of the strips containing such capsules does not cause any leakage or breakage of such capsules. Instead, the design of capsules is such that they are frangible with a considerable amount of force being directly applied thereto once the strips are placed on the nail surface, as described above. In certain embodiments, once positioned as described above, the outside foil material is grasped by the user's other hand/fingers (or instead by a salon assistant) and pressure applied downward, toward the nail surface, is applied in a fashion so as to pop or otherwise rupture the capsule structure, thus permitting the solvent contained therein to be released in a fashion sufficient to be absorbed by the surrounding absorbent material. The amount of force required to achieve this breakage of the capsule may vary, but preferably is about the same amount required for a person to break a bubble-wrap bubble by pressing down thereon. The capsule can be manufactured in a fashion such the one or more portions thereof are intentionally designed to be weaker than surrounding material, thus facilitating a more directional fracture of the capsule. For example, the capsule may have one weaker side being glued or placed next to the absorbent material, with the opposing side closer to the foil surface being more robust and stronger, upon which a person applies pressure, thus causing the weaker region of the capsule to burst first, and release of the solvent then being better directed to the absorbent material, rather than to other regions of the strip, e.g. toward the adhesive regions on some strips where one would prefer solvent to be directed away from.

In still other embodiments, the fracturing of the capsule of solvent can be achieved in any other effective and desired manner, such as by providing a sharpened aspect of the foil wrap material such that when pressed, the sharpened aspect is directed toward the capsule so that the capsule is punctured, thus releasing the solvent inside.

In one embodiment where two materials are to be released (such as the solvent to remove nail polish and a color change agent), a divider may be employed that may comprise a membrane having one or more zones of weakness, such as a declivity or score line, such that when the hollow body is bent, pressed, crushed, flexed, or compressed along the zone of weakness, an opening is created in the divider, permitting the contents of the first compartment and the second compartment to mix. In other embodiments, one or more puncture tips may be provided along an inner surface of the hollow body retaining the solvent, color change agent, etc. When a compressive, bending or flexing force is applied against the puncture tips, the tips puncturely engage the divider and form an opening therein, permitting the contents to saturate the absorbent material. The hollow body that holds the solvent, color change agent, etc. is preferably manufactured from a gas and liquid impermeable, heat sealable material that is suitable for thermal bonding or sonic welding. This material is preferably flexible—or at least crushable via manual compression, so that the user will be able to manually manipulate the contents of the compartments. An exemplary material is commercially available Mylar-polyethylene barrier layer material. Other suitable materials include high-density polyethylene, polypropylene, polystyrene, polyvinylchloride, and the like. Suitable materials for making liquid impermeable film include polyolefins, such as polyethylene and polypropylene; polyvinyl acetate; and the like. The absorbent material and the solvent containing reservoir may be joined to the by such means as adhesives, ultrasonic welding, heat bonding, and the like.

The hollow body preferably has an opening at a first end, and a frangible seal that closes the opening to retain the contents housed in the hollow body. In one embodiment, the frangible seal comprises a thin membrane, for example, thin films of plastic or aluminum foil can be heat sealed to the hollow body to cover the opening in the first end. Upon bending the walls of the hollow body at or near the frangible seal, the seal is broken. In another embodiment, the frangible seal comprises a cover having a zone of weakness, such as one or more score lines so that when a compression force is applied near the cover, the score lines are broken, permitting fluid to pass therethrough. Other exemplary frangible seals are disclosed in Truhan, U.S. Pat. No. 3,759,259 and U.S. Patent Publication No. 20120148636 to Berrido et al.—which are incorporated herein by this reference.

An absorbent material preferably is of a known type, including but not limited to cotton fibers or synthetic fibers, such as plastic fibers, or a semi-porous material, such as a sponge, preferably ones that are acetone resistant. When the frangible seal is broken, the contents of the hollow body are released into the absorbent material. Suitable substrate materials for the nail contacting portion of the strip have been described herein, but may include woven fabrics, non-woven fabrics, gauze, foams, sponges and the like.

The hollow interior of the solvent containing member defines a reservoir for containing a liquid composition, such as the solvent, color change material, etc. and at least its proximal and distal ends are sealed to provide a liquid tight seal. Preferably, a frangible seal is provided at distal end that is liquid-tight prior to use of the strip. The frangible seal is designed to preferably be weaker than the seal at its proximal end., thus when the solvent containing capsule is manipulated, for example by squeezing with the fingers causing the frangible seal to be broken, permitting the solvent or other liquid material in the reservoir can flow out. The plastic at the distal end of the stick may be first thinned out and then sealed to provide frangible seal. Suitable designs for material employing a hollow reservoir for use in the present invention are known in the art and are taught, for example, in U.S. Pat. No. 5,100,028, the disclosure of which is hereby incorporated by reference, albeit that the reservoirs are preferably smaller to enclose them in the absorbent material of the strip. The reservoir material be made of any suitable material including, but not limited to, plastics such as polyethylene, polypropylene, foil, and the like. The size of the liquid reservoir is sufficient to retain enough liquid for accomplishing the desired function of nail polish removal, gel removal, shellac remover, etc. Still other patents that are incorporated herein by this reference are U.S. Pat. No. 7,008,392 to Beaudry; U.S. Pat. No. 8,696,227 to Carter; U.S. Pat. No. 4,740,194 to Barabino; and U.S. Pat. No. 7,025,521 to Tsaur, showing how various embodiments can be made.

While embodiments of the invention have been described in detail with respect to the application of removing nail polish, gels, artificial nails, etc, one of skill in the art will appreciate that the novel and nonobvious aspects as described have applications in other areas and endeavors, such as in providing a variety of desired substances in association with an absorbent layer via employment of a frangible capsule that can contain such substance in association with an adhesive portion so that the substance can be administered to the desired site. Thus, for example, a band-aid-like structure can be used in association with a capsule containing aloe or another wound healing substance, or a pain killer, an allergesic, a medicine, a growth promoting material, a cosmetic, a lotion, a muscle treatment gel, bug repellent, deodorant, antiperspirant, etc. such that the affected area can be covered with an adhesive bandage and then at a desired time, the capsule associated with e absorbent material can be broken to release the desired pre-packaged substance or combination of substances. In one particular embodiment, the use of a capsule is employed that can contain more than one substance separated by frangible structures such that a combination of substances can be delivered in a desired sequence and in a particular position on a surface, such as a person's skin, so that the purposeful combination of such substances can be achieved in an easy fashion. The strips of the present invention, by virtue of their encapsulated frangible structures associated with absorbent materials and barriers (either to retain solvent material from vaporizing into the air freely, or conversely, a barrier on the opposite side of the absorbent material such that the material in the encapsulated structure is precluded from contacting an underlying surface and is instead, free to vaporize) find various uses that are accomplished in an easy, cost effective manner and enables one to carry the devices with them for use outside of professional salons, medical clinics, etc.

One particular aspect of the present invention is directed to the field of insect repellents and specifically to personal area repellents. Thus, instead of acetone being encapsulated in a portion suitable for the removal of nails when the capsule is broken, insect repellent substances are encapsulated in a frangible shell such that release of such material upon the selection of the user and in a fashion that can prevent substantial skin contact with the insect repellent, is made possible. In certain embodiments, the present invention is directed to an adhesive patch or strip that can be contacted to a person's body and that has an insect repellent capsule associated with the absorbent material that has (and preferably is surrounded by) adhesive material designed to contact a wearer's skin. Thus, in one embodiment, a band-aid-like product is provided that has a capsule having insect repellent encapsulated in a reservoir wherein the encapsulation is within a frangible enclosure that is in contact with an absorbent material, such that when the capsule is broken, the insect repellent material soaks the absorbent material and thus permits the repellent to emanate its vapors, and thus protection, from the site where the band-aid has been attached. Preferably a skin barrier is provided such that the insect repellent material does not contact the person's skin, but rather the barrier supports the layer of encapsulated insect repellent such that when the frangible encapsulation is broken, the material soaks absorbent material ontop of the barrier, and the insect repellent can then vaporize into the air surrounding the strip. For written and enablement support for various features included in the present invention, the following is hereby incorporated herein by this reference: US Patent publication No. 20060226249 to Ketcha, et al.

Known methods for delivering insect repellents in a manner which is safe and efficacious tend to be dangerous, short-acting and inconvenient. One method by which consumers protect themselves from insect bites and insect landings is the use of topical repellents. Many topical repellents contain N,N-diethyl-m-toluamide ("DEET") as the active ingredient. Topical repellents contain relatively high amounts of insect repellent that can be absorbed into the bloodstream through the skin. Therefore, it is an object of this invention to provide a method and device for repelling insects by providing a more convenient, cost effective, user-friendly and effective device and method for repelling insects as compared to the use of topical repellents in lotion or spray-on form.

DEET (N,N-diethyl-m-toluamide) is a versatile and effective insect repellent that has been used for more than 40 years by millions of people worldwide to repel mosquitoes, ticks, fleas, biting flies and chiggers. Most bug repellents contain DEET because DEET is one of the few insect repellents that work. It is recommended to prevent mosquito-born diseases such as malaria, dengue fever, and West Nile virus. Other less effective repellents contain pyrethrins, a pesticide created from the chrysanthemum flower; neem leaf extract, neem oil, citronella and geraniol. Persons applying DEET to their skin may get hives or have mild redness and irritation. These symptoms are usually mild and will go away when the product is removed from the skin. Persons who use very high concentrations of DEET on their skin over a long period of time (such as military personnel or game wardens) may have more severe skin reactions that include blistering, burning, and permanent scars of the skin. Other symptoms associated with long-term use of high amounts of DEET (over 50% concentration) include insomnia and mood changes. By far, the most serious and devastating complication of large DEET poisonings is neurological damage. Patients may have disorientation, clumsiness when walking, seizures, or coma. Death is possible in these cases. Users of DEET are warned to not apply it over cuts, wounds or irritated skin; to avoid spraying DEET on plastics (such as watch crystals and eyeglasses frames), rayon, spandex, other synthetic fabrics, leather and painted or varnished surfaces, because DEET can damage those surfaces. While typically effective, DEET products must be reapplied after several hours. Due to the problems it can present to humans, despite its effectiveness as a repellent, DEET is typically employed at rather low concentrations, with a concentration of 10% to 30% used according to the directions on the product labels.

Among the drawbacks of DEET are that it possesses an unpleasant odor and imparts a greasy feel to the skin. Although it has recently been re-registered for use in the US by the EPA, concerns have been raised as to its safety, particularly when applied to children. Studies have demonstrated that high concentrations of DEET may give rise to allergic or toxic reactions in some individuals. Other disadvantages associated with DEET include that it (1) is a synthetic chemical having a limited spectrum of activity; (2) is a powerful plasticizer and will dissolve or mar many plastics and painted surfaces; and (3) plasticizes the inert ingredients typically used in topical formulations in order to lengthen the time of effectiveness. This leads to DEET formulations with low user acceptability.

Recent clinical observations have shown that DEET insect repellent can cause severe central nervous system toxicity and even death from skin penetration. This is a particularly significant problem for children who have larger body surface area-to-mass ratios and higher skin permeability. Additionally, children tend to lick their fingers and hands, which can cause them to ingest the insect repellents. Because insect repellents are removed by skin absorption, evaporation, perspiration, and through participation in water activities, it must be reapplied at frequent intervals. The requirement for frequent reapplications results in a continual threat of systemic toxicity to the user. The present invention provides a way to safely and effectively achieve insect repellent results without applying the active compound directly to the skin.

In various embodiments dealing with the encapsulation of an insect repellent, the wearer of the adhesive device or strip preferably avoids having their skin directly contacted with a topical repellent material, but at the same time, benefits from having the repellent very close to the skin of the wearer, thus achieving the benefits of having the vapors that repel insects, while not experiencing the topical absorption of insect repellent that is believed to be less than desirable from a health standpoint. Thus, in some embodiments, there is provided a barrier (e.g. a foil or plastic film or layer) between the absorbent layer and the skin of a person such that the encapsulated insect repellent, once the insect repellent capsule is broken and soaks the absorbent material, does not contact the skin of the wearer of the adhesive strip. Instead, the breakage of the frangible enclosure of insect repellent causes the absorbent material to become somewhat saturated in a manner that permits the insect repellent to relatively slowly evaporate and cause protective vapors to surround the skin of the wearer of the strip, thus providing insect repellent protection without the user experiencing any of the potentially harmful effects derived from a topical application of the insect repellent materials.

It is an object of certain embodiments of the present invention to provide a wearable personal protection device that can be worn on a person and that rely on passive evaporation of the insect repellent out of a carrier impregnated therewith. Repellents may include DEET, geraniol, citronella, limonene, and pyrethroids such as allethrin.

The insect repellent strips of the present invention are advantageous over topical compositions for several reasons, including that they are more convenient in that they do not require the time consuming task of applying lotion or a spray to clothing and exposed skin. The wearable strips offer similar advantages to those of topical compositions without the drawbacks, as they provide protection wherever the subject goes, as would a topical composition when applied correctly.

Personal insect repellents, such as DEET-containing lotions and sprays, are commonly applied directly to the skin of a user and are recognized as efficacious when so used. Some users, however, find such a treatment to be aesthetically unsatisfactory. There exist treated wrist bands, patches and other treated materials to be worn or otherwise applied to a user's skin or clothing to repel mosquitoes, many employing citronella as a repellent, such as in U.S. Pat. No. 5,656,282, (incorporated herein by this reference) which teaches the use of patches attachable to clothing or limbs that disperse citronella. Use of transfluthrin, vaporthrin, and/or DDVP to control insects via passive evaporation is known in the context of room insect control. See e.g. U.S. Pat. Nos. 6,582,714; and 6,534,079, also incorporated herein in their entireties by this reference. Similarly, publication 2004/0134999 (incorporated herein by this reference) teaches the use of metofluthrin or profluthrin to passively evaporate and control insects for room control.

In certain embodiments of the present invention, dihydronepetalactone compositions are employed in the encapsulated structures described herein in addition to or in place of DEET compositions, as such dihydronepetalactone compositions perform well as a new class of effective insect repellent compounds without the disadvantageous properties characteristic of prior-art compositions.

In particular embodiments, insect repellents that may be encapsulated and then employed on the strips of the present invention include the following: a dihydronepetalactone, or a mixture of dihydronepetalactone stereoisomers, an aliphatic alcohol; a component selected from the group consisting of (i) one or more members of the group consisting of (AI) cyclo(ethoxy) methicone, (BI) bisphenyl hexamethicone, (CI) $C_{24}$~$C_{28}$ alkyl methicone, and (DI) cetyl dimethicone polyol; (ii) one or more members of the group consisting of (AII) glycol ricinoleate, (BII) polyglyceryl ricinoleate, (CII) propylene glycol ricinoleate, and (DII) glyceryl ricinoleate; and (iii) octyldodecanol; a component (d) that comprises a $C_{50}$~$C_{650}$ branched polyhydroxy polyoxyethylene/polyoxypropylene block copolymer of ethylene diamine; a component (e) that comprises (i) a mixture of butylene glycol, propylene glycol and methyl propanediol, and/or (ii) a mixture of glycerol, methyl propanediol and isostearyl neopentanoate; and a component (f)

that comprises one or more members of the group consisting of aminobenzoic acid, glyceryl aminobenzoic acid, oxybenzone, sulisobenzone, dioxybenzone and titanium dioxide.

In addition to DEET or in its place, various embodiments of compositions that may be encapsulated and used on strips of the present invention include picaridin, with 5%-15% picaridin formulas being found comparable in effectiveness (2-6 hours) to low-concentration DEET; and natural repellents made from plants, e.g. oil of lemon eucalyptus, citronella, and soybean/geranium oils. Other effective insect repellents such as permethrin can be applied to clothing—but not to a person's skin. Permethrin works mainly by killing ticks that come in contact with it and exposure should be minimized. Various compositions can be employed as insect repellents and thus, encapsulated together or separately (e.g. to provide choices for individuals as to type of substance they wish to employ via breaking frangible encapsulations; dosage and timing of administration of an insect repellent). Thus, one aspect of the invention involves the provision of an insect repellent strip (which should be understood in various embodiments to comprise a patch—rather than any rectangular-limited shaped product) having one or more encapsulated insect repellent containing formulations that when released onto an absorbent material—(i.e. after the encapsulated structure is broken)—a person is provided with an amount of insect repellent in a selectively desirable time period and in a desired amount. Thus, certain embodiments include more than one frangible encapsulated portion of an insect repellent, such as DEET, so that if one desires a higher concentration and/or increased volume of material, or on a more frequent administration regime, to be made available to the absorbent material of a strip as described herein, they can selectively compress and break such enclosed capsules to release desired and pre-determined amounts of the insect repellent for the particular occasion. For example, if someone is trekking through a mosquito infested area for several hours and requires reapplication of a DEET containing formulation to achieve desired protection, but also desires to avoid skin contact with DEET products, then the ability to simply break one of several DEET containing capsules at a desired time period, thus permitting the DEET material to soak the adjacent absorbent material, and then provide the protection due to the vapors evolving from the now soaked absorbent material, is an effective way to achieve insect repellent results without undue skin exposure to DEET. The strips or patches may be stick-on patches, or may be in the form of wrist, ankle, arm or leg bands, or may be in the form of pendants or medallions. The insect repellent strips of the present invention are suitable to dispense at least 0.01 mg of insect repellent per hour at 25.degree. C. in still air conditions. In certain embodiments, the insect repellent encapsulated within the one or more capsules (which preferably each contain at least about 0.25 ml of an insect repellent composition), includes a pyrethroid insect repellent selected from the group consisting of transfluthrin, metofluthrin, and profluthrin. The total amount of said insect repellent so applied is an amount effective to provide practical mosquito personal area repellency. Preferably insect repellent is provided in at least 0.5 ml encapsulated enclosures that are designed to be frangible upon a person compressing such structures to cause the release of the contents thereof, preferably being then absorbed onto the adjacent absorbent material.

To comply with written description and enablement requirements, incorporated by reference in their entireties are the following: U.S. Patent Publications and Patents: 20130095162 to Quinn, U.S. Pat. No. 5,591,820 to Bastar; U.S. Pat. No. 6,865,444 to Howard; 2002-0160035 to Fotinos; U.S. Pat. No. 5,455,043 to Fischel-Ghodsian; 20060188538 to Emmrich et. al.; U.S. Pat. No. 8,748,477 to Scialdone; and 2002 0160035 to Kim.

In preferred embodiments, the strip includes absorbent material suitable to restrain the insect repellent once released from a frangible enclosure, such as a substrate formed from a material selected from the group consisting of polypropylene, polyethylene, polyester, nylon, rayon, cellulose acetate, wood pulp and cotton, and other non-woven fabrics which may be spunbonded, spunlaced, spunlaid, melt blown, needle punched, hydroentangled, latex bonded, and/or resin bonded.

The insect repellent strips may be placed at a variety of locations, such as around wrists or ankles, near the shoulders or chest, along the calves or lower limbs, or on clothing adjacent to these positions.

In one embodiment, the insect repellent strip is comprised of a multi-layer structure, with an upper impregnatable non-woven fiber material layer adjacent to one or more encapsulated structures containing the insect repellent, an adhesive layer, and a peel-off layer. Preferably, there is a barrier between the insect repellent encapsulated material and the skin of a user, such that no undesired contact with insect relent transpires. In other words, a person achieves protection from insects without exposing themselves to having insect repellent contact their skin directly, but instead, are able to apply adhesive strips that both protect the skin from insect repellent while also providing the advantages attained by having insect repellent on top of the particular skin surface.

The strips are of a type that can be readily and inexpensively manufactured. Further, they are of a size and weight that a consumer would tolerate wearing. When the insect (preferably mosquito) repellent strips are used, after the release of the encapsulated repellent into the adjacent absorbent material, one achieves the vapors that are believed responsible for the mosquito-repelling effect. The mosquito strips can also be applied to walls, furniture, tents, and household appliances and can provide good mosquito-repelling effect.

Thus, in one embodiment, the insect repellent strip includes a pre-sized strip for adhesive engagement with a person's skin or clothing, such strip having an adhesive portion that is configured to contact the skin or clothing to hold such strip in place, where the strip has at least four layers, with a first layer comprising an exterior odor impervious material, a second layer that comprises one of encapsulated insect repellent, a third layer having an insect repellent absorbent layer, and a fourth layer having a peelable backing; and wherein the insect repellent is encapsulated in a frangible shell.

Certain advantages of use of the present invention include the ability of a user to apply a strip to areas of their body desired to be protected at some time and the later deployment of the insect repellent via the purposeful breakage of at least one of the encapsulated capsules present on a strip so as to achieve the maximum protection with freshly provided repellent. The manner in which the frangible capsule can be broken, e.g. with either a finger compressing the capsule sufficiently hard downwardly against the skin surface upon which the strip is adhered to; by employment of a non-body part, such as a pencil or other hard object by which to achieve the compressive force necessary to break the capsule and thus release the insect repellent into the absorbent material of the strip, etc., can vary. Importantly, however, it is possible for a user of the strip to avoid any hand contact, and certainly at least any substantial hand contact, with the insect repellent whatsoever, but still achieve employment of the freshly activated and available insect repellent by breaking one or more frangible encapsulated enclosures of the insect repellent. Thus, the dosage (e.g. via breaking one, two, three or more frangible encapsulations of insect repellent); and the timing of administration/employment of insect repellent, is provided as an available option for a user. In certain situations such options that avoid the necessity of having to use one's hands to physically contact insect repellent lotions or creams to rub over parts of one's body to achieve insect repellent protection is critical, such as when an outdoorsman is involved in other activities that do not readily permit the rubbing of lotions on body parts. Thus, a white water rafter, a mountain rope climber, a hunter, etc. by using the present invention, are able to simply cause one or more frangible encapsulations to break that are pre-positioned on the person's wrist, arm, ankles, thighs, etc., when actively engaged in other sporting/paddling/hunting activities where having to either spray a can of insect repellent or rub lotion on body parts would be not only inconvenient, but perhaps dangerous.

In certain other aspects of the present invention, embodiments include the use of encapsulated substances in addition to insect repellent that one may wish to employ at either the same time or at different times for different purposes. For example, different dosages or concentrations of an insect repellent may be desired at different times of day. A lighter dose of certain repellents may be desired in the morning when certain insects may not be a problem, but a heavier dose or a completely different formulation of repellent, may be desired at a different time of day when certain insects may be more active. The wearer of a strip may also desire to have a certain perfume aspect available to mask the smell and odor of certain repellents, and thus, the breaking of one or more encapsulations that contain a perfume or cyclodetrin component to mask or eliminate certain odors is made possible by the present invention. Strips can be made that include different sized encapsulations (e.g. volumetric amounts) such that not only the type of substance can be selected to be released from such frangible enclosures, but the user may select the volume of such substance to release at any time.

The present invention also finds application in the companion pet field and veterinary field. The strips of the present invention provide the ability to associate strips to pet collars or to other regions of a pet's body (e.g. around a leg, on its hair, etc.) to provide the ability to include various desired substances in encapsulated form such that the pet owner can break a frangible encapsulation of such desired material to protect its pet from particular diseases, such as those associated with tics, etc. In one embodiment the strip is comprised of a layered article comprising: an adhesive layer; and an insect repellent layer that is encapsulated in one or more of the encapsulation structures as set forth herein, and may further include a copolymer, an ethyl cellulose, and a thermoplastic polyurethane. Incorporated herein by this reference in its entirety is US patent publication no. 20130251773 for particular time release compositions that may be employed. Flea and tick repellent and insecticides may be encapsulated as herein described and provided on a strip such that the strips can be incorporated in pet collars, thus permitting the release of the active insect repellent agents onto the pet while the pet is wearing the collar to help control fleas and ticks which come into contact with the animal. Such collars are particularly adaptable for pets (or for horses, etc.) because it is difficult to apply insect repellents and insecticides to animal skin and fur on a regular basis. To further comply with written description and enablement requirements, incorporated by reference in their entireties are the following US patents and publications: 20130095162 to Quinn, U.S. Pat. No. 5,591,820 to Bastar; U.S. Pat. No. 6,865,444 to Howard; 20020160035 to Fotinos; U.S. Pat. No. 5,455,043 to Fischel-Ghodsian; 20060188538 to Emmrich et al.; U.S. Pat. No. 8,748,477 to Scialdone; 20120264788 to Ecker et al.; and 20020160035 to Kim.

In a particular embodiments, the frangible encapsulated enclosures of repellent material (although there can be other agents so encapsulated) may be present in a volume that exceeds some of the other embodiments described above with respect to the preferably 0.5 ml and 1 ml amounts. Thus, volumes of 2 ml, 4 ml, 10 ml or greater may be achieved to suit the particular application and need. For example, if the strip is to be used for a small dog on its collar, it may only require one or just a few milliliters of active repellent ingredients. If a large horse is involved, however, a far greater volume of repellent may be required and desired to have the desired effect of protecting the animal from insects.

Various embodiments will also employ a color change agent to display to a pet owner (or in some embodiments the person wearing such strip) that the strip's frangible capsule has been broken. Still other color change agents may be used to indicate the length of time that the device has been employed, for example, how long the repellent has been broken out of (freed) from its frangible shell, such that a pet owner can decide to either replace the strip or to break another of the unbroken frangible encapsulations on the strip associated with the animal. A series of frangible encapsulations can thus be provided on any strip such that the dose, type or frequency of administration of an agent encapsulated thereby can be released. Certain strips may have different sized and different volume of encapsulations on the same strip to permit a selection of dosage; type of repellent employed at a given time, etc. Thus, in one example, a strip may have a DEET encapsulated frangible shell as well as a non-DEET insect repellent, such the user (or pat owner) may select which particular agent to employ at any given time.

Another aspect of the present invention is directed to the encapsulation of bioluminescent material in a manner such that the frangible capsule(s) can be active to trigger bioluminescent illumination upon fracturing of the frangible shell, thus releasing the material into preferably the absorbent material. As one will appreciate, however, in other embodiments the bioluminescent material may be simply constrained in another enclosure after the underlying frangible capsule is broken (thus triggering the activation of the bioluminescent material, such that the bioluminescent material will slosh around yet another enclosure on the strip, but without the use of any absorbent material).

One particular use of the strip embodiments that contain a bioluminescent capsule, is that a pet owner can choose to break both a capsule filled with an insect repellent, as well as break a capsule on the same strip that contains bioluminescent material, thus providing the pet with protection from some insects, and at the same time being visible at night for a certain period of time (e.g. until the bioluminescent material expires is illumination abilities.) Certain other embodiments include just the provision of a strip with one or more frangible capsules of bioluminescent material that a pet owner, a parent of a child going treat or treating on Halloween, etc. can selectively determine what illumination is desired via the breakage of more than one capsule provided on the strip. Different colored bioluminescent material may be provided on individual strips, or may be provided in individual capsules containing such different materials on a single strip, thus permitting some individual selection of what colors of bioluminescent materials to display at any given time. Either bioluminescent, photo luminescent, fluorescent, chemiluminescent or phosphorescent materials, or a combination thereof, can be employed as useful in the present invention, as each of such substances can be encapsulated in a manner that when the frangible encapsulation is broken, the illuminating aspects of the material enclosed in the frangible shell can luminescence. For written description and enablement support for various embodiments, the following are incorporated herein by this reference in their entireties: U.S. Pat. No. 7,980,203 to Rubottom; 20130247841 to Stoffels, et al,; and U.S. Pat. No. 6,394,040 to Axel.

In certain embodiments, the encapsulated, frangible enclosures resemble in some respects so-called blister-packaging, with desired material within such "blisters" selected from the group of acetone, solvents, chemiluminescent material, glow-in-the-dark material, perfumes, deodorants, masking agents, color change agents, hunting scents that conceal a hunter's natural body odor from a hunted animal, and insect repellents. One of skill in the art will appreciate, however, that still numerous other compounds, substances, chemicals, etc. of various uses can be included in various embodiments of the present invention, especially those that require desired temporal release of material into an absorbent material so that such material either remains in contact with a desired surface for per-determined amount of time, or alternatively, is permitted to evaporate or vaporize into the surrounding atmosphere so as to distribute the desired agent for the purpose at hand. In one particular embodiment, an extract of the mushroom L. squarrosulus having p53 tumor combating abilities is employed. For example, with respect to blister-type packages, the blisters can be pressed on to cause a fracture thereof, thus releasing the enclosed material into absorbent material, another less frangible enclosure, etc.

Desired material to encapsulate, such as perfumes, insect repellents, solvents, etc. are often expensive and generally less cost effective when employed at high levels in personal care compositions, cleaning compositions, and protective chemical agents for humans or pets. As a result, there is a desire to maximize the effectiveness of such desired materials. One method of achieving such an objective is to improve the delivery efficiency and active lifetime of the desired material. This can be achieved by providing the desired material as a component of a microcapsule. Microcapsules provide several benefits. They have the benefit of protecting the desired material from physical or chemical reactions with incompatible ingredients in the composition, volatilization or evaporation. Microcapsules have the further advantage in that they can deliver the desired material to the substrate and can be designed to rupture under desired conditions. Microcapsules are made either by supporting the desired material on a water-insoluble porous carrier or by encapsulating the desired material in a water-insoluble shell. In the latter category microencapsulates are made by precipitation and deposition of polymers at the interface, such as in coacervates, for example as disclosed in US Patent publication 20110152159; GB-A-0 751 600, U.S. Pat. No. 3,341,466 and EP-A-0 385 534, or other polymerisation routes such as interfacial condensation U.S. Pat. No. 3,577,515, US-A-2003/0125222, U.S. Pat. No. 6,020,066, WO2003/101606, U.S. Pat. No. 5,066,419. A particularly useful means of encapsulation is using the melamine/urea-formaldehyde condensation reaction as described in U.S. Pat. Nos. 3,516,941, 5,066,419 and 5,154, 842, all of the above references which are incorporated herein in their entireties by this reference. Such capsules are made by first emulsifying a desired material in small droplets in a pre-condensate medium obtained by the reaction of melamine/urea and formaldehyde and then allowing the polymerisation reaction to proceed along with precipitation at the oil-water interface. The encapsulates range in size from a few micrometer to a millimeter are then obtained in a suspension form in an aqueous medium. The microcapsules preferably comprise a nominal shell to core mass ratio lower than 15%, preferably lower than 10% and most preferably lower than 5%. Hence, the microcapsules may have extremely thin and frangible shells. The compositions of the present invention may be encapsulated within a water-soluble film. The water-soluble film may be made from polyvinyl alcohol or other suitable variations, carboxy methyl cellulose, cellulose derivatives, starch, modified starch, sugars, PEG, waxes, or combinations thereof. In another embodiment the water-soluble film may include a co-polymer of vinyl alcohol and a carboxylic acid. The water-soluble film herein may also comprise ingredients other than the polymer or polymer material. For example, it may be beneficial to add plasticisers, for example glycerol, ethylene glycol, diethyleneglycol, propane diol, 2-methyl-1,3-propane diol, sorbitol and mixtures thereof, additional water, disintegrating aids, fillers, anti-foaming agents, emulsifying/dispersing agents, and/or anti-blocking agents.

One will appreciate that this summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, pictures, etc. will provide a basis for the scope of the present invention as it may be claimed now and in future applications.

BRIEF DESCRIPTION OF THE DRAWINGS

FIG. 3 is an illustration of a pre-made sheet of fingernail strips that can be dissociated with the sheet and individually applied to fingernails.

FIG. 4 is a side view of one embodiment of a strip where an outer layer precludes escape of vapors emanating from the nail polish removing agent; the adhesive layer or portion is adjacent the other side's protective and removable layer, and the nail polish removing agent is contained there between.

FIG. 5 is a side view of one embodiment where polish removing agent is encapsulated into small beads.

DETAILED DESCRIPTION OF CERTAIN PREFERRED EMBODIMENTS

Figure 1:
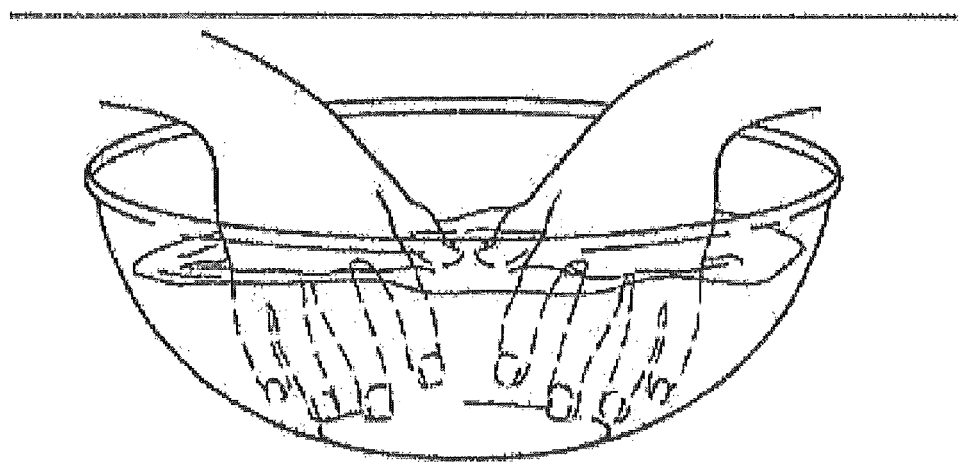
FIG. 1 is a view of prior art methods of removing fingernail polish.
Figure 2:
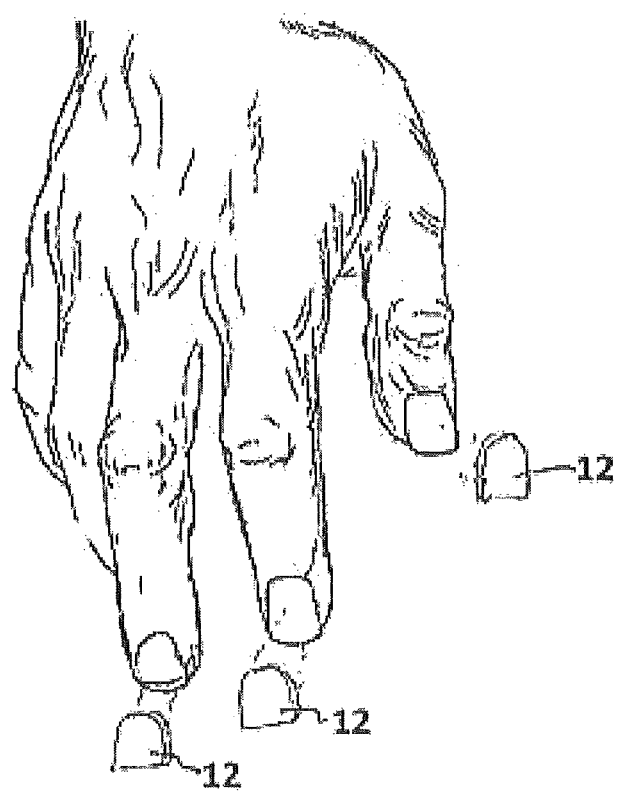
FIG. 2 is a perspective view of a fingernail with an adhesively associated strip of the present invention.
Figure 6:
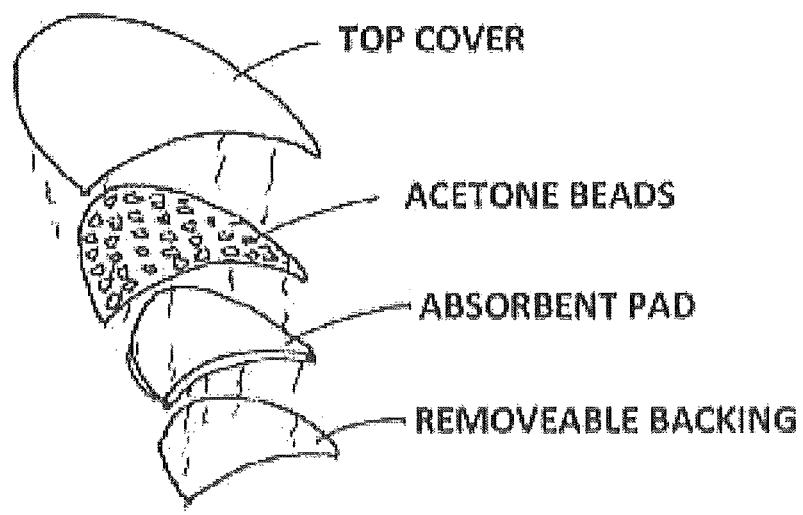
FIG. 6 is an exploded view of one embodiment of the present invention showing a top cover, a layer of acetone beads, an absorbent pad beneath the same and a removable backing associated therewith.
Figure 7:
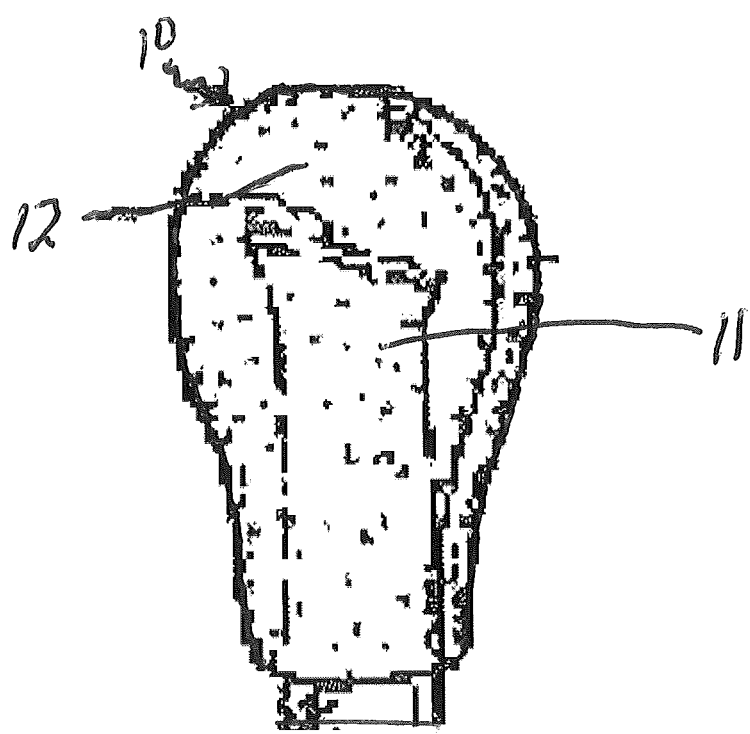
FIG. 7 is one embodiment showing an encapsulation of a material substance inside a frangible inner container, surrounded by absorbent material, e.g. a popule embodiment.
Figure 8:
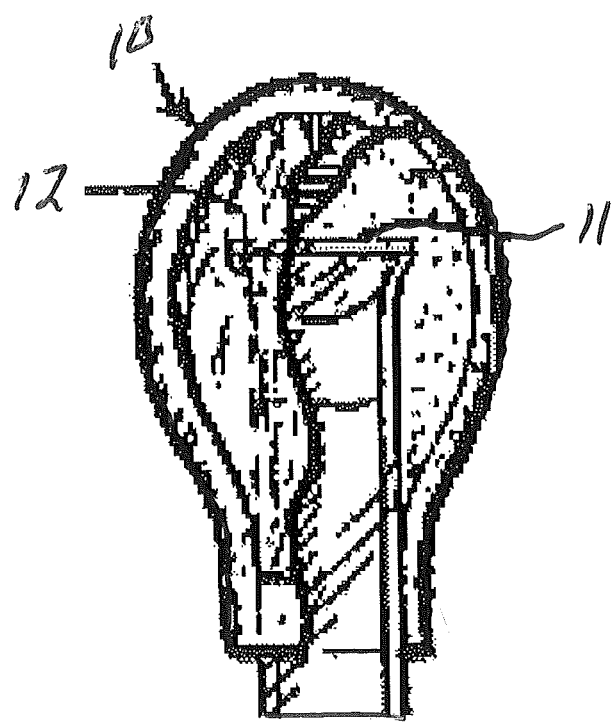
FIG. 8 is another embodiment of a frangible capsule/ampule with an absorbent covering
Figure 9:
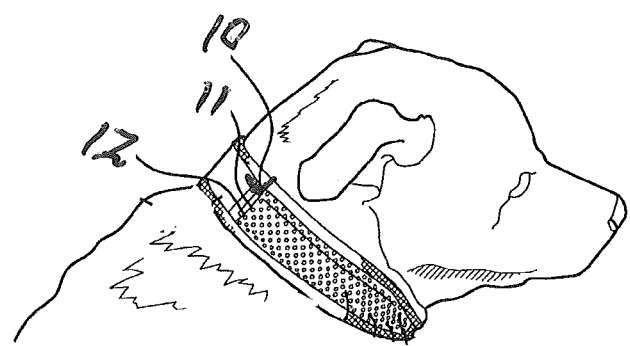
FIG. 9 is a schematic drawing showing the head portion of a dog wearing a collar having a strip according to the present invention.
Figure 10:
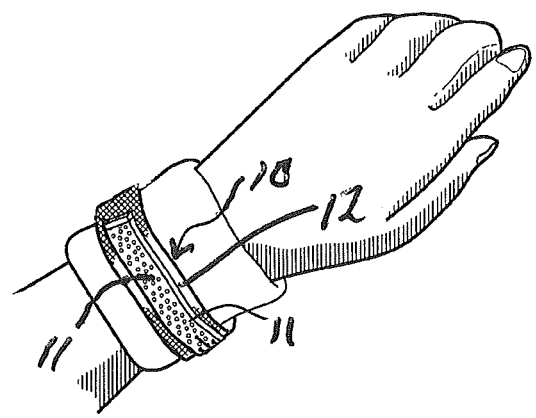
FIG. 10 is a schematic drawing showing the wrist and hand portion of a person wearing a wristband with a strip according to the present invention.
Figure 11:
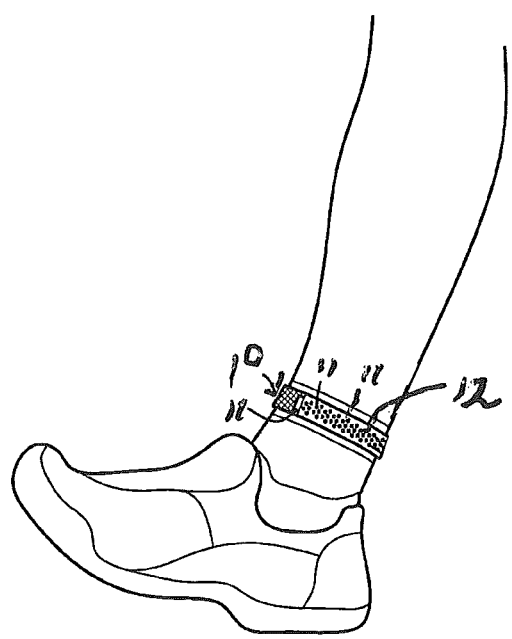
FIG. 11 is a schematic drawing showing the lower leg and foot portion of a person wearing an ankle band with a strip according to the present invention.
Figure 12:
FIG. 12 is a schematic drawing showing the upper body portion of a person wearing a shirt with a repellent pocket strip according to the present invention.
Figure 13:
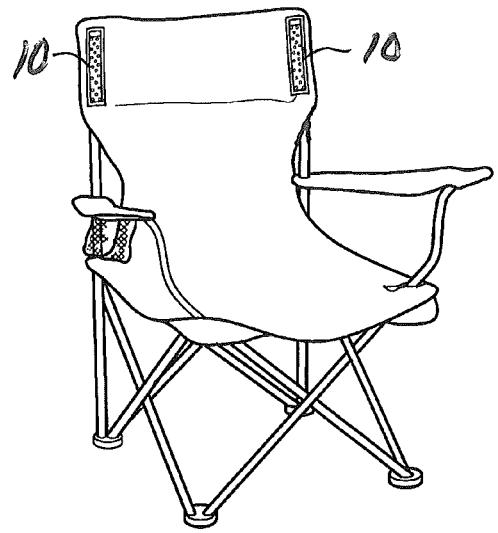
FIG. 13 is a schematic drawing showing a chair with strips according to the present invention.
Figure 14:
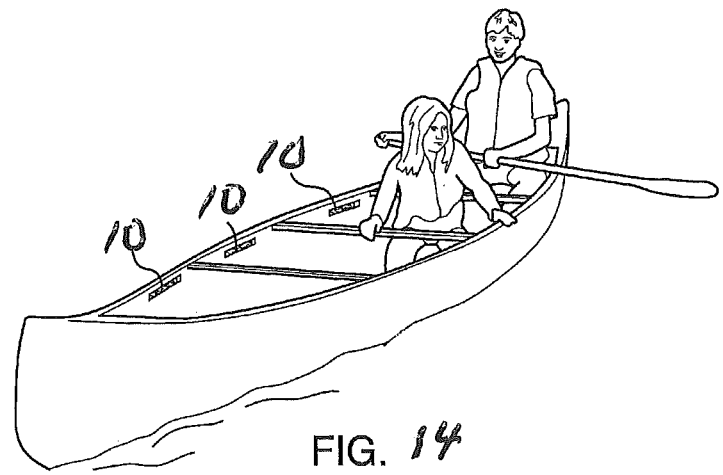
FIG. 14 is a schematic drawing showing a canoe with strips attached according to the present invention.
Figure 15:
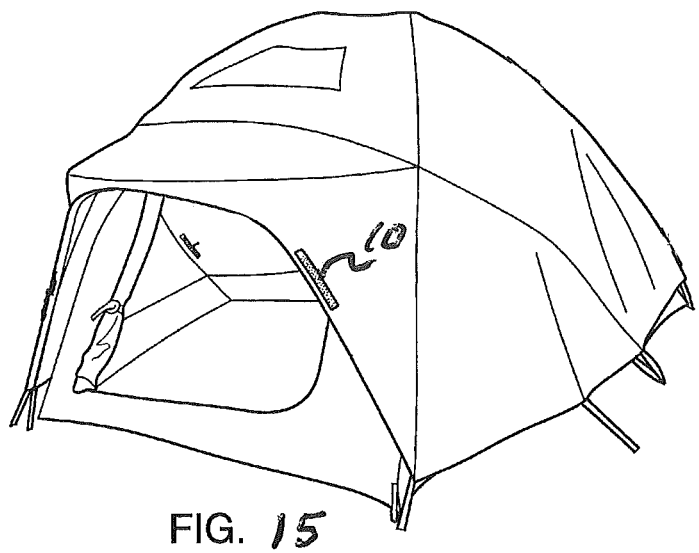
FIG. 15 is a schematic drawing showing a tent with strips attached according to the present invention.

The present invention is generally a nail polish removal system shown in the figures. The system 10 includes multiple strips having associated pads impregnated with either an acetone-based or non-acetone based solvent that is effective at dissolving nail polish. Depending on what types of nails are put in contact with the pads 12, such as natural or synthetic nails, the type of solvent to be applied is significant. Although other solvent formulations are contemplated by the present invention, the solvent formulation of the preferred embodiment is preferably acetone based, as it has outperformed most non-acetone based formulations, However, the present invention is not limited to the use of acetone containing formulations and includes, for example, other formulations including a mixture of methylacetyl, dimethylketal, and deionized water. A feature of the present invention is the use of an effective amount of solvent in combination with pads 12 to achieve removal of nail polish with the amount of solvent with which pads 12 are impregnated preferably being predetermined and controlled so that excess solvent does not create droplets or spillage from pads 12.

Strips are preferably sized and shaped to match up with a person's fingernails or toenails, and as such, different sized versions of pre-fabricated strips are contemplated as a best mode for distribution and use. Preferably the strips are relatively thin and include a pad having a diameter of at least 7.5 centimeters. The thickness of pads 12 is sufficient to contain the amount of polish removing solvent, and thus may vary due to the particular solvent used. In most embodiments, however, the strips and associated pads are preferably between 0.5 millimeter and 3 millimeters, more preferably less than about 2 millimeters, and more preferably less than 1 millimeter. Although other types of fabrics or materials are contemplated, such as cotton based materials, pads 12 are preferably made of spunlaced fabric. The use of spunlaced fabric avoids fibers or filaments from becoming attached to the nails during the nail polish removal process, which can thereafter hinder smooth polishing and/or require additional labor to achieve clean nails. Furthermore, the spunlaced fabric is soft and pliable. These features enhance the nail polish removal process because the user can more easily manipulate the pads to effectively and accurately remove the nail polish.

The dimensions of pads are predetermined to easily cover the entire nail to achieve maximum contact between the impregnated solvent and the nail. It will be apparent to those skilled in the art of nail polish removal systems that many modifications and substitutions can be made to the preferred embodiment described above without departing from the spirit and scope of the present invention.

One particularly desirable aspect of many of the embodiments of the present invention is the reduction in undesired odor or fumes arising from the conventional or typical methods used to remove finger and toe-mail polish and artificial nails. For example, the covering provided that overlies the saturated pads of nail-polish removing formulations precludes a significant amount of vapors form otherwise being evaporated into the air, thus reducing the air around the nail customer, as well as the nail clinician, from breathing in such fumes. This has an especially advantageous safety aspect to various embodiments of the present invention. More than one odor-reducing layer can be employed and the various embodiments may employ at least two, at least three or at least four separate layers of material over-lying the absorbent pad material that contains the nail polish removing agents. Such layers may be of the same or similar material, or may be selected for their distinct properties, such as flexibility, ability to avoid having odorous materials from passing there through; their porosity; their color, brittleness; degradability, etc. In certain embodiments, the nail polish removing agent is in a gelled or semi-solid state such that it does not drip or move from the strip/pad, but rather remains adhered to the same so that it can be placed or positioned appropriately on a nail surface, where it can contain and direct nail polish remover to the nail surface to dissolve the layer of polish thereon.

In various embodiments, the nail removal strips or tabs are provided with an easily gripped, packet of individual or multiple tabs/strips such that the protective backing of each tab (or a set thereof) is able to be removed to expose the adhesive bonding surface that is itself associated with the nail polish removing surface of the nail polish removal device.

In other embodiments, the nail-polish removing agent can be encapsulated in a frangible shell or small enclosure so that it is not released in a fashion that can be absorbed by the pad fabric or other material until desired. Thus, as shown in some of the figures, small acetone containing beads 11 can be provided between two layers, with an upper layer being of a substantially order impervious material and the lower material of the lower layer being removable so that when it is, the beads are amenable to being broken or fractured, thus releasing their contents onto both the nail surface and or into an adjacent absorbent pad, such pad associated with the top layer.

For ease of complying with written description and enablement requirements, the following references are incorporated herein in their entireties, especially as it relates the various acetone-based and non-acetone based compounds and solutions and formulations that can be employed in various embodiments of the present invention: U.S. Pat. No. 5,823,203 to Carroll et al., U.S. Pat. No. 6,367,485 to Dutton-Davis et al.; 20030127104 to Tyre; 20060283470 to Keogh; 20070107745 to Kiyomoto; 20070287647 to Hadry; 20080142405 to Knapp; 20100204076 to CHENG; 20100305491 to Baschnagel; 20080060550 to MacDonald; U.S. Pat. No. 7,806,877 to Kang et al.; U.S. Pat. No. 4,800,904 to Kinseley et al.; U.S. Pat. No. 4,619,253 to Anhauser et al.; U.S. Pat. No. 5,924,428 to Song; U.S. Pat. No. 6,990,985 to Allen et al.; U.S. Pat. No. 6,060,073 to Keller; and U.S. Pat. Nos. 5,415,903 and 5,525,389 to Hoffman et al. Also incorporated by reference herein in their entireties are the following issued patents and published applications: 20040142830 to Tavares; 20080039812 to Kang; U.S. Pat. No. 4,696,393 to Laipply.

In one embodiment, the present invention includes a nail cover of a material sized to proximate the size of a user's fingertip or toenail and configured to have a top wall, a bottom wall and an inside surface further comprising adhesive disposed on at least a portion thereof to contact the a nail. In other embodiments, the strips of the present invention include a self-adhesive laminate, shapeable to toe and fingernails, containing a film-forming polymer layer containing at least one plasticizer, a pressure-sensitive adhesive layer located thereon, and a carrier film which covers the pressure-sensitive adhesive layer and can be removed.

In still other embodiments, the present invention includes a transfer adhesive sheet that has a series of precut areas of transfer adhesive for applying a predetermined nail shape to a person's nail. The transfer adhesive tabs may be fabricated as sheet material that includes an adhesive protected by a bottom layer liners positioned on the side of the adhesive, such as adhesives used in securing false plastic finger nail. Preferably the adhesive is just around the periphery of the nail region and more preferably is adhesive that is less adhesive than the adhesives used to adhere fake fingernails to nails (e.g. because the adhesive must merely be sufficient to hold the strips/tabs of the present invention in contact with the nail until the nail polish removing agent can dissolve the polish it contacts, e.g. about 1-2 minutes, more preferably at least about 3 minutes and less than about 10 minutes. Methods of producing such sheet material of transfer adhesive tabs will be apparent (with the guidance herein provided) to those of skill in the art but include the steps of applying an adhesive layer to the surface of a first material—which may be associated with the pad that is to be saturated with acetone or like material. The sheet material may be manufactured in small pieces or in a long piece formed into a roll. Roll material is generally manufactured in a continuous process which is typically more economical than making small pieces such as letter or A4 size or other sizes. The roll can be cut into such smaller sizes if desired. The protective substrate will preferably easily peel away from the adhesive. Preferably the maximum adhesive is on such sheets is five thousandths of an inch and having a thickness about one-half of one thousandth of an inch. In other embodiments, however, the thickness of the pad beneath the outer layer protective layer is fairly thick (like a dime or a penny) to facilitate the absorbance and retention of a sufficient amount of nail polish removing material.

One aspect of various embodiments relates to the use of a solubilized mixture composed of an electron-donating color-developing organic compound selected from pyridines, quinazolines, and bisquinozolines; an electron-accepting compound serving as a color-developer for the above compound; and a reaction medium for coloring and the above compound in a specified temperature range. Such compositions develop fluorescent color of yellow, yellowish orange, orange, reddish orange, or red with a high color density and high color brightness, yet gives no residual color under non-color-developing conditions, and has remarkably improved light resistance. In this regard, color changing embodiments that can be used with the present invention include those set forth in U.S. Pat. No. 5,558,700 to Shibahashi et al., incorporated herein by this reference.

In other embodiments, there is a desire to have the odor of acetone or even non-acetone agents reduced. To accomplish the same, certain embodiments incorporate odour-eliminating products with Cyclodextrins or more preferably, modified β Cyclodextrin as one of its main ingredients. A Febreze-like component can be associated with the strips to achieve the desired deodorization process, which in some embodiments, involve the entrapment of malodour molecules when they complex with Cyclodextrin and are effectively retained to keep their concentration in the air low. This decreases the volatility of the malodour molecules and causes odour elimination. In a preferred embodiment, hydroxypropyl beta-cyclodextrin or HPβCD is employed for such purpose, with such component being preferably associated with the absorbent pad of the strip, such that it is released and active when the nail polish removing agent is released.

It will be appreciated that various know color changing components can be employed such that the breakage of encapsulated or micro-encapsulated beads of one agent is then made available to react with another agent, which may be, for example, impregnated onto the absorbent pad. Thus, one can fine tune and select appropriate color change times by the selection of reactive chemicals that provide a desired color change at a certain time—preferably about 3-10 minutes after application of the strip to the nail.

In terms of a method, in one embodiment a sheet as described above is selected with appropriate pre-determined fingernail or toenail perforated portions. The individual nail contacting portions are then detached from the sheet and the protective bottom laminate is removed to expose the nail contacting surface, i.e. the saturated (or bead containing) pad that is contacted with the polished portion of the person's nail. Preferably there is at least a portion, such as a preferably, of the strip that maintains the strip in place on the nail during a period of at least 30 seconds, more preferably for at least about 2 minutes and more preferably for up to about 10 minutes. This time should be sufficient for the nail polish removing substances employed to dissolve the polish. At such time the strips can be removed from the nail surface and excess or dissolved polish can be further removed with a cloth, tissue or cotton balls. The use of the strips, however, reduces the amount of odor emanating from the person's treated nails as the top-most protective layer of the strip precludes the free evaporation of such acetone or nail polish remover substance.

As designed, a device and method embodying the teachings of the present invention is easily applied. The foregoing description is included to illustrate the operation of the preferred embodiment and is not meant to limit the scope of the invention. As one can envision, an individual skilled in the relevant art, in conjunction with the present teachings, would be capable of incorporating many minor modifications that are anticipated within this disclosure. Therefore, the scope of the invention is to be broadly limited only by the following claims.

What is claimed is:

1. A nail polish remover strip, comprising:
 a pre-sized strip for one of a toenail or a fingernail, having an adhesive portion around a periphery of the strip that is configured to contact just a periphery of a user's fingernail or toenail, said strip adapted to be applied to a fingernail or toenail having nail polish thereon, and left in contact with a user's fingernail or toenail for a predetermined period of time to dissolve the nail polish thereon, said strip having at least four layers, with a first layer comprising an exterior odor impervious material, a second layer that comprises one of encapsulated acetone or an encapsulated nail polish removing agent, a third layer having a solvent absorbent layer, and a fourth layer having a peelable backing;
 a color change indicator included between said first layer and said peelable backing that is adapted to produce, after at least 10 minutes of contact between the strip and the polished nail, a color change sufficient to indicate to the person that a predetermined dwelling time has transpired;
 wherein the adhesive portion is sufficient to hold the strip in contact with the fingernail or toe nail until the acetone or nail polish removing agent dissolves polish present on said user's nail; and
 wherein the acetone or nail-polish removing agent is encapsulated in a frangible enclosure.

2. The nail polish remover strip as set forth in claim 1, wherein at least two of said pre-sized strips are provided across from each other on a sheet.

3. The nail polish remover strip as set forth in claim 1, wherein the strip is sized so that it does not encompass a user's finger opposite the user's nail.

4. The nail polish remover strip as set forth in claim 1, wherein the strips have a thickness of between 0.5 millimeter and 3 millimeters.

5. The nail polish remover strip of claim 1, wherein said nail polish removing agent comprises isobutyl nitrite.

6. The nail polish remover strip of claim 1, wherein said color change indicator is not directly associated with a chemical reaction with one of said nail polish removing agent or acetone.

7. A method for removal of artificial nail extensions from a user's natural nails, said method comprising the steps:
   a) selecting a fingernail removal strip sized to approximate the size of a user's fingernail and configured to have a top layer comprising a material substantially impervious to acetone, a lower removable protective layer, and an absorbent pad layer located below the top layer and above the removable lower protective layer; and a frangible, solvent-containing enclosure associated with said absorbent pad layer; said strip having pressure-sensitive adhesive disposed on at least a portion around a periphery of the strip to maintain said strip in position on a person's fingernail for at least 3 minutes, said strip having at least one odor reducing component;
   b) contacting said strip to a user's fingernail such that said adhesive is in contact with a periphery of the user's fingernail;
   c) pressing on said frangible, solvent-containing enclosure to release said solvent;
   d) retaining said strip on the user's fingernail for a time period of at least 3 minutes; and
   e) removing said strip after at least 3 minutes, wherein the solvent on said absorbent pad removes an artificial nail extension from a user's natural nails and wherein said strip is sized so that it does not encompass a user's finger opposite the user's nail.

8. The method as set forth in claim 7, wherein the strips have a thickness of between 0.5 millimeter and 3 millimeters.

9. The method as set forth in claim 7, wherein said nail polish remover strip comprises a color change indicator included between said top layer and said lower removable protective layer that is adapted to produce, after at least five minutes of contact between the strip and the polished nail, a color change sufficient to indicate to the user that a predetermined dwelling time has transpired.

10. The method as set forth in claim 9, wherein said color change indicator is not directly associated with a chemical reaction with one of said nail polish removing agent or acetone.

11. The method as set forth in claim 7, wherein the strips have a thickness of between 0.5 millimeter and 3 millimeters.

12. A method for removal of artificial nail extensions from a user's natural nails, said method comprising the steps: providing a sheet having a plurality of pre-determined fingernail perforated portions formed as individual strips, said sheet formed into a roll; pulling on the sheet to rotate the roll; removing an individual fingernail contacting perforated portion from said roll to provide an individual strip having a protective layer that reduces the evaporation of acetone and that is substantially impervious to acetone; removing a protective laminate associated with said strip to expose a contacting surface consisting of an absorbent pad, said absorbent pad having an acetone containing layer adapted to retain an amount of acetone sufficient to remove an artificial nail extension from a user's natural nails, the absorbent pad located below the protective layer, said strip having an adhesive portion around a periphery of said strip; positioning said strip onto a person's nail such that the adhesive portion contacts a periphery of a user's nail; pressing the strip onto the user's nail in a fashion such that the acetone containing layer is compressed to release acetone onto the absorbent pad; maintaining the strip in place on the user's nail for a period of time lasting at least 30 seconds and removing the strip from the user's nail.

13. The method as set forth in claim 12, wherein said step of maintaining comprises retaining said strip on the user's fingernail for a time period of at least 3 minutes, wherein the acetone on said absorbent pad removes an artificial nail extension from a user's natural nails.

14. The method as set forth in claim 12, wherein at least two strips are provided across from each other on said sheet.

15. The method as set forth in claim 12, wherein the strips have a thickness of between 0.5 millimeter and 3 millimeters.

16. The method as set forth in claim 12, wherein said step of positioning results in only a user's nail being covered and does not encompass a user's finger opposite the user's nail.

17. The method as set forth in claim 12, further comprising removing said strip from a user's nail when a color change indicator produces, after at least five minutes of contact between the strip and the polished nail, a color change sufficient to indicate to the user that a predetermined dwelling time has transpired.

18. The method as set forth in claim 12, wherein said step of pressing causes a frangible enclosure of acetone to break.

* * * * *